(12) United States Patent
Haber

(10) Patent No.: US 9,429,523 B2
(45) Date of Patent: Aug. 30, 2016

(54) METHOD AND APPARATUS FOR THE DETECTION OF EXPLOSIVES

(71) Applicant: American Innovations, Inc., Chestnut Ridge, NY (US)

(72) Inventor: Grant Haber, Spring Valley, NY (US)

(73) Assignee: AMERICAN INNOVATIONS, INC., Chestnut Ridge, NY (US)

( * ) Notice: Subject to any disclaimer, the term of this patent is extended or adjusted under 35 U.S.C. 154(b) by 449 days.

(21) Appl. No.: 13/890,609

(22) Filed: May 9, 2013

(65) Prior Publication Data

US 2015/0268171 A1 Sep. 24, 2015

(51) Int. Cl.
| | |
|---|---|
| *G01N 21/78* | (2006.01) |
| *G01N 21/75* | (2006.01) |
| *G01N 33/20* | (2006.01) |
| *G01N 31/22* | (2006.01) |
| *G01N 33/22* | (2006.01) |
| *G01N 21/77* | (2006.01) |

(52) U.S. Cl.
CPC ............ *G01N 21/78* (2013.01); *G01N 31/227* (2013.01); *G01N 33/227* (2013.01); *G01N 2021/7759* (2013.01); *Y10T 436/173076* (2015.01); *Y10T 436/193333* (2015.01)

(58) Field of Classification Search
CPC ...................... G01N 33/0337; G01N 33/0036; G01N 33/0027; G01N 33/0009; G01N 33/0004; G01N 33/00; G01N 31/005; G01N 31/227; G01N 31/00; G01N 31/22; Y10T 436/17; Y10T 436/173076; Y10T 436/00

USPC .................................. 436/110, 106, 107, 125
See application file for complete search history.

(56) References Cited

U.S. PATENT DOCUMENTS

| | | | | |
|---|---|---|---|---|
| 5,620,658 A | * | 4/1997 | Jaunakais | G01N 31/22 422/401 |
| 6,087,089 A | * | 7/2000 | Wu | C12Q 1/00 423/582 |

FOREIGN PATENT DOCUMENTS

| | | | | |
|---|---|---|---|---|
| WO | WO 2006/079167 A1 | * | 8/2006 | ............ G01N 21/78 |
| WO | WO 2013/001534 A1 | * | 1/2013 | ............ G01N 21/76 |

OTHER PUBLICATIONS

International Search Report for WO 2015/016997 A3, Method and Apparatus for the Detectino of Explosives, search completed on Dec. 24, 2014, obtained on Sep. 2, 2015, pp. 1-3.*

* cited by examiner

*Primary Examiner* — Christine T Mui
(74) *Attorney, Agent, or Firm* — Ladas & Parry LLP

(57) ABSTRACT

A method for the colorimetric detection of two compounds in a bulk sample comprises the steps of forming an aqueous solution of the bulk sample, inserting a single dip strip having a pair of test regions each having separate colorimetric indicator reagents for a different one of the two compounds to be tested for into the solution and then removing the dip strip from the solution, and observing the test regions for color changes denoting the presence of the two compounds. The methodology is especially adapted for the colorimetric detection of nitrates and chlorates, two components commonly associated with explosives and particularly homemade explosives.

7 Claims, 1 Drawing Sheet

METHOD AND APPARATUS FOR THE DETECTION OF EXPLOSIVES

The present invention relates to a method for the calorimetric detection of explosives, and especially for the detection of certain precursors, associated with explosives and particularly with homemade explosives (HMEs), and an apparatus in the form of a kit for carrying out the method.

BACKGROUND OF THE INVENTION

The detection of explosives has always been of great interest and concern to both the military as well to the civilian police. With the expansion of terrorist organizations and others constructing explosive devices in makeshift labs and with readily-available materials, the need to detect such devices, as well as their precursor components, is of vital importance to the safety and protection of both military and civilian personnel.

Many HMEs, (along with other explosives) utilize nitrates or chlorates as active components. While tests for such compounds are known, and there are test kits that utilize reagents that detect such components, there remains a need for a methodology that can be applied in the field, by relatively untrained personnel, and which provides a clear colorimetric indication of the presence of such components. For such field use the incorporation of additional tests for other precursors, with the added complexity and bulk required for such tests, is not needed.

Accordingly, there remains a need for a methodology that can be incorporated into a kit that is convenient and simple to use, and which can provide rapid and accurate indications of the presence of nitrates and chlorates under a variety of field conditions.

BRIEF DESCRIPTION OF THE INVENTION

In accordance with the above, the present invention comprises a kit having a vial into which a sample to be tested for nitrates and chlorates can be placed. Water is included in the vial or added to the vial to dissolve the sample, and a colorimetric dip strip is dipped into the solution. The dip strip contains two discrete sections, one having a colorimetric indicator for nitrate, and the other having a colorimetric indicator for chlorate. The nitrate indicator may be based on one of the known colorimetric reactions, such as a Griess reaction, while the chlorate indicator may likewise be based on a known colorimetric reaction therefor, such as a starch-iodine reaction. The reactants are present on the dip strip in solid form, and are activated when the strip is dipped into water. When subsequently placed in contact with a solution bearing either a nitrate and/or a chlorate, the respective colorimetric reaction occurs, with the section of the dip strip bearing the respective reagents changing color to indicate the presence of the nitrate or chlorate.

BRIEF DESCRIPTION OF THE DRAWINGS

A fuller understanding of the present invention will be obtained upon review of the following detailed description of illustrative embodiments thereof, in conjunction with the accompanying drawings, wherein.

DETAILED DESCRIPTION OF THE INVENTION

Figure 1:
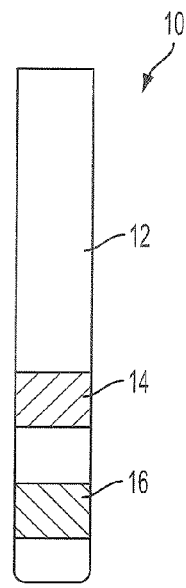
FIG. 1 is a front view of a dip strip bearing the reagents required for carrying out the method.

FIG. 1 illustrates a dip strip for use in connection with the present invention. Dip strip 10 comprises a base 12 of an elongated shape, the lower portion carrying two reagent-bearing areas 14 and 16, each for the indication of one of nitrate and chlorate. The upper portion of the dip strip base serves as a handle. As known, the base may be of a suitable rigid or semi-rigid material, non-reactive with solutions of the compounds intended to be tested. Preferable materials are plastic compositions. Each of the reagent-bearing areas 14 and 16 is in the form of a sheet or pad of an absorbent material, capable of holding the indicator reagents in a dry form. Such materials may include filter paper, nonwoven and woven fabrics, hydrophilic polymer sheets and other otherwise suitable, inert porous materials. The back surface of the absorbent material may be attached to the base by a suitable adhesive.

The reagent-bearing areas 14 and 16 are each saturated with an indicator solution chosen to be responsive to the presence of one of nitrate and chlorate in solution. The indicator reagents for nitrate may preferably be a set for carrying out a Griess reaction, which is a diazo-coupling color reaction. As known, nitrate ions present in a solution to be tested are reduced by zinc to nitrite. An acid solution of sulfanilic acid and alpha-naphthylamine will undergo a diazotization reaction with the nitrite, forming a red azo dye. The nitrate-testing pad is thus prepared by the application of zinc particles along with a sulfanilic acid alpha-naphthylamine solution to the respective one of the areas 14 or 16 and allowed to dry, the zinc particles being retained by the fibrous nature of the pad in combination with the dried acid solution.

The reagents in the other of the areas 14 and 16 are preferably for performing a starch-iodine reaction, and include an iodide, typically present in the form of potassium iodide, and starch. The iodide, when oxidized, converts to iodine/triiodide, which reacts with the starch to generate a blue-black indication. Starch granules may be mixed with a potassium iodide solution, and the pad saturated with the mixture and allowed to dry. Chlorate when present in a test solution provided the starting material for the needed iodide oxidizer.

The dip strip, with the pads bearing the dry reagent compositions, remains stable and unreactive until the pads are wet. Thus the dip strips are well suite for field use. The strips may be packaged in a waterproof container for such use.

The steps of the inventive process may be carried out through the provision of a kit of test components, comprising a testing vial with or without water, a dry dip strip, and a small quantity of a further reagent, as discussed below, preferably provided in a dropper vial or bottle. The components themselves may be packaged in a box, bag or pouch for convenient personal transport.

Figure 2:
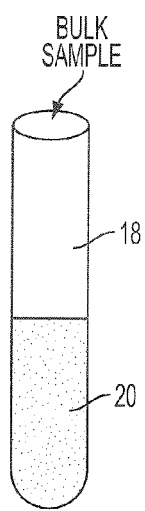
FIGS. 2-5 are diagrammatic representations of the steps of the method.

In a first step a small quantity of the bulk sample to be tested, on the order of 0.25 grams, is added to purified water, as depicted in FIG. 2. Preferably the water 20 is provided in a sealed testing vial 18, which is opened, the sample added, and the vial reclosed and agitated to place the sample into solution.

Figure 3:
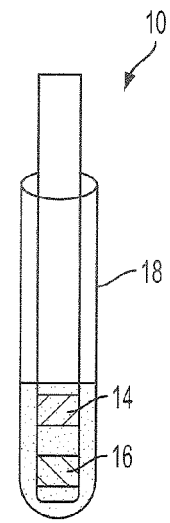

In a second step (FIG. 3), the vial is reopened and the dip strip inserted into the vial to wet the reagent areas with the test solution and rapidly removed. The strip can be gently shaken to remove excess liquid and avoid the possible presence of a liquid bridge between the pads and comingling of the respective reagents. Use of a hydrophilic material for the strip base can further insure that there is no passage of liquid between the pads. At this time the nitrate indicating reagents begin reacting with any present nitrate for generation of the telltale red color.

Figure 4:
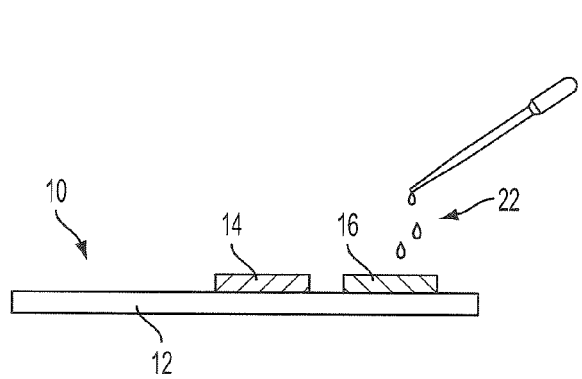

As depicted in FIG. 4, in a third step a 6N solution 22 of hydrochloric acid is applied in a drop wise fashion to the pad bearing the chlorate test reagents. The acid converts any present chlorate to chlorine, which serves as the oxidizer for the iodate, resulting in formation of the blue-black indicator.

Figure 5:
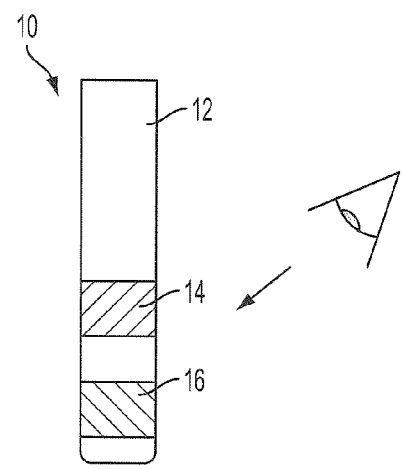

In a fourth step (FIG. 5) the dip strip is observed to determine if any color indication has been generated, indicating the presence of nitrate and/or chlorate in the sample, suggesting the presence of an explosive compound or a precursor compound therefor.

While the present methodology has been described in connection with performing a test for the presence of nitrate and chlorate, an analogous series of steps may be performed for the simultaneous testing of other pairs of compounds. The required respective calorimetric reagents are carried in a dry form on the pads, such that they are activated upon dipping into a solution of the substance to be tested. After dipping and removal a further reagent may be applied to one or both pads as may be required to complete the indicator reactions. The dip stick pads are then visually observed for any color indication for the tested components.

I claim:

1. A method for the colorimetric detection of two compounds in a bulk sample, comprising the steps of:
    forming an aqueous solution of the bulk sample;
    inserting a single dip strip having a pair of test regions each having separate colorimetric indicator reagents for a different one of the two compounds to be tested for into the solution and then removing the dip strip from the solution and then removing the dip strip from the solution, wherein a first of the test regions comprises colorimetric indicator reagents for detecting nitrate ions that may be present in the solution by reducing the nitrate ions to nitrite and causing a diazotization reaction with the nitrite to form an azo dye, and a second of the test regions comprises colorimetric indicator reagents comprising (i) an iodide that is oxidized by chlorate ions that may be present in the solution to form iodine/triiodide and (ii) a starch; and
    observing the test regions for color changes denoting the presence of the two compounds.

2. The method of claim 1, further comprising the step of applying a further reagent to at least one of the test regions after the dip strip is removed from the solution.

3. The method of claim 2, wherein the colorimetric indicator reagents for detecting the nitrate are Griess reaction reagents.

4. The method of claim 2, wherein the colorimetric indicator reagents for detecting the chlorate ions are starch-iodide test reagents and the further reagent is hydrochloric acid which is applied to the second test region.

5. The method of claim 2, wherein the colorimetric indicator reagents for detecting the nitrate and chlorate ions are in dry form before the dip strip is inserted into the bulk sample solution.

6. The method of claim 5 wherein the colorimetric indicator reagents are compounded in solution form, applied to the respective test regions and allowed to dry before the dip strip is inserted into the bulk sample solution.

7. The method of claim 2, wherein the aqueous solution of the bulk sample is formed by providing a covered vial of water, uncovering the vial and dissolving a test sample of the bulk sample in the water in the vial, and the step of inserting the dip strip into the solution is performed by inserting the dip strip into the vial.

* * * * *